United States Patent
Samchukov et al.

(10) Patent No.: US 11,812,995 B2
(45) Date of Patent: *Nov. 14, 2023

(54) EXTERNAL FIXATION CONNECTION ROD WITH FEMALE ATTACHMENT

(71) Applicant: Texas Scottish Rite Hospital for Children, Dallas, TX (US)

(72) Inventors: Mikhail L. Samchukov, Coppell, TX (US); John D. Ross, Ovilla, TX (US); Alexander M. Cherkashin, Flower Mound, TX (US)

(73) Assignee: TEXAS SCOTTISH RITE HOSPITAL FOR CHILDREN, Dallas, TX (US)

(*) Notice: Subject to any disclaimer, the term of this patent is extended or adjusted under 35 U.S.C. 154(b) by 573 days.

This patent is subject to a terminal disclaimer.

(21) Appl. No.: 16/945,350

(22) Filed: Jul. 31, 2020

(65) Prior Publication Data

US 2020/0360057 A1    Nov. 19, 2020

Related U.S. Application Data

(63) Continuation of application No. 16/020,623, filed on Jun. 27, 2018, now Pat. No. 10,743,918.

(51) Int. Cl.
| | |
|---|---|
| *A61B 17/62* | (2006.01) |
| *A61B 17/66* | (2006.01) |
| *A61F 5/042* | (2006.01) |
| *A61B 17/00* | (2006.01) |
| *A61B 17/56* | (2006.01) |

(52) U.S. Cl.
CPC .............. *A61B 17/66* (2013.01); *A61B 17/62* (2013.01); *A61F 5/042* (2013.01); *A61B 2017/00991* (2013.01); *A61B 2017/564* (2013.01)

(58) Field of Classification Search
CPC ................. A61B 17/66; A61B 17/62; A61B 2017/00991; A61B 2017/564; A61F 5/042
USPC ........................................ 606/56, 57
See application file for complete search history.

(56) References Cited

U.S. PATENT DOCUMENTS

| | | | |
|---|---|---|---|
| 2,346,346 | A | 4/1944 | Anderson |
| 4,621,627 | A | 11/1986 | DeBastiani |
| 5,382,248 | A | 1/1995 | Jacobson et al. |
| 8,439,914 | B2 | 5/2013 | Ross |
| 8,444,644 | B2 | 5/2013 | Ross |
| 8,574,232 | B1 | 11/2013 | Ross |
| 9,078,700 | B2 | 7/2015 | Ross |
| 9,456,849 | B2 | 10/2016 | Ross |
| 9,788,861 | B2 | 10/2017 | Murray |
| 9,827,011 | B2 | 11/2017 | Cresina |
| 9,936,975 | B2 | 4/2018 | Siemer |
| 10,010,350 | B2 | 7/2018 | Mannanal |

(Continued)

*Primary Examiner* — Eduardo C Robert
*Assistant Examiner* — David C Comstock
(74) *Attorney, Agent, or Firm* — Haynes and Boone, LLP

(57) ABSTRACT

A connecting rod for an external fixation device includes a first joint having a first rotatable member housing, a first rotatable member disposed within the first rotatable member housing, and a first connecting member. The first rotatable member has a first bore. The first connecting member includes a first connecting member insert having a stem partially disposed within the first bore of the first rotatable member. The first connecting member insert includes a second bore. The second bore is operable to receive a connecting element from a first external fixation ring.

20 Claims, 10 Drawing Sheets

(56) References Cited

U.S. PATENT DOCUMENTS

| | | | |
|---|---|---|---|
| 10,082,384 B1* | 9/2018 | Singh | A61B 34/10 |
| 10,743,918 B2* | 8/2020 | Samchukov | A61B 17/66 |
| 2007/0049930 A1 | 3/2007 | Heam et al. | |
| 2011/0118738 A1* | 5/2011 | Vasta | A61B 17/62 |
| | | | 606/56 |
| 2011/0208187 A1 | 8/2011 | Wong | |
| 2013/0123784 A1 | 5/2013 | Ross | |
| 2013/0253513 A1 | 9/2013 | Ross | |
| 2014/0135764 A1 | 5/2014 | Ross et al. | |
| 2015/0148846 A1 | 5/2015 | Jackson | |
| 2015/0265313 A1 | 9/2015 | Wong | |
| 2015/0305776 A1* | 10/2015 | Ross | A61B 17/60 |
| | | | 606/56 |
| 2015/0313641 A1 | 11/2015 | Ross | |
| 2016/0278812 A1* | 9/2016 | Riccione | A61B 17/62 |
| 2018/0368887 A1 | 12/2018 | Lauf | |

* cited by examiner

EXTERNAL FIXATION CONNECTION ROD WITH FEMALE ATTACHMENT

CROSS REFERENCE TO RELATED APPLICATIONS

The present application is a continuation of U.S. patent application Ser. No. 16/020,623, filed Jun. 27, 2018, now U.S. Pat. No. 10,743,918, which is hereby incorporated by reference in its entirety.

TECHNICAL FIELD

The present disclosure relates, in some embodiments, to the field of external fixation, and more specifically, to connection rods having an adjustment mechanism that allows for rapid and/or gradual adjustment of an overall length of the connection rods.

BACKGROUND OF THE DISCLOSURE

Without limiting the scope of the disclosure, this background section is described in connection with external fixation devices and specifically connection rods. Generally, external fixation devices are commonly used in a variety of surgical procedures including limb lengthening, deformity correction, fracture reduction and treatment of non-unions, mal-unions and bone defects. The process involves a rigid framework comprising one or more rings that are placed externally around the limb and attached to bone segments using wires and half pins inserted into the bone segments and connected to the related section of the external rigid framework. The opposite rings of the rigid framework are interconnected by either threaded or telescopic rods directly or in conjunction with hinges or ball joints, which allow the surgeon to connect opposite rings that are not parallel to each other after manipulation with bone segments either rapidly (acutely) or gradually over a period of time.

For example, in bone fracture reduction or non-union treatment, the wires and half pins are inserted into each bone segment and attached to rings of a rigid framework. The rigid framework is used to acutely reduce a displacement and restore alignment between the bone segments. During the realignment of the bone segments, the orientations of opposite rings often are not parallel. Those opposite rings of the rigid framework are connected together by threaded and/or telescopic rods with attached hinges or ball joints. This allows the opposite bone segment to be rigidly fixed until complete fracture healing or bone consolidation is completed.

The hinges or ball joints may have a male or female connection mechanism in order to facilitate coupling of the threaded or telescopic rods to the fixation rings. For example, a male connection mechanism may have a protruding connection element, e.g., short threaded rod or socket, for insertion into a receiving portion of a fixation ring. On the other hand, a female connection mechanism may receive a connection element, e.g., screw or bolt, from a fixation ring.

SUMMARY

The present enclosure includes embodiments of an external fixation connection rod that allows for rapid, coarse adjustments and/or gradual, fine adjustments of the rod length, and is operable to be easily and rigidly attached to non-parallel external fixator rings.

In some embodiments, a connecting rod for an external fixation device may comprise a telescopic housing comprising a proximal end, a distal end, and a first axial bore at least partially extending from the distal end to the proximal end, the first axial bore defining a first lengthwise axis; an inner sleeve slidably disposed within the first axial bore of the telescopic housing; a fastener operable to releasably couple the inner sleeve and the telescopic housing; an elongated member coupled to the inner sleeve; a first joint comprising a first rotatable member housing coupled to the proximal end of the telescopic housing; a first rotatable member disposed within the first rotatable member housing; and a first connecting member comprising a first connecting member insert coupled with the first rotatable member; wherein the first connecting member insert comprises a second axial bore defining a second lengthwise axis; and wherein the second axial bore is operable to receive a connecting element from an external fixation ring; and a second joint comprising a second rotatable member housing coupled to the elongated member; a second rotatable member disposed within the second rotatable member housing; and a second connecting member coupled with the second rotatable member, wherein the second connecting member is operable to couple with an external fixation ring; and wherein at least one of the first and second joints comprises one or more grooves defined in the wall of the respective rotatable member housing, and the respective connecting member is disposed through one or more grooves, thereby limiting the rotation of the respective rotatable member in a first direction about the joint while allowing a greater range of motion in a second direction about the joint; and wherein the rotational movement of the first and second rotatable members is limited upon fixation of the respective connecting member to an external fixation ring.

In some embodiments, the first connecting member further comprises a first connecting member housing comprising a first aperture and a non-circular cavity, and the first connecting member insert further comprises a non-circular portion operable to rotationally couple with the non-circular cavity about the second lengthwise axis after insertion of the first connecting member insert through the first aperture.

In some embodiments, the first connecting member housing comprises at least one of a tool manipulation facilitator and a manual manipulation facilitator.

In some embodiments, the connecting member housing comprises a coupling facilitator on the coupling end of the connecting member housing.

In some embodiments, the connecting member housing comprises an inner recessed portion near the base, the inner recessed portion formed complementarily to the first rotatable member housing.

In some embodiments, the first rotatable member is inserted into the first rotatable member housing through the first axial bore of the telescopic housing and an aperture defined in the base of the first rotatable member housing.

In some embodiments, the first connecting member insert is threadably coupled with the first rotatable member. In some embodiments, the second connecting member comprises a second connecting member insert, the second connecting member insert comprising a third axial bore defining a third lengthwise axis, and wherein the third axial bore is operable to receive a connecting member from an external fixation ring.

In some embodiments, the inner sleeve comprises an internally threaded fourth axial bore operable to couple with the elongated member, and wherein the elongated member is operable to translate relative to the inner sleeve about the first lengthwise axis, upon rotation of the elongated member relative to the inner sleeve about the first lengthwise axis.

In some embodiments, one rotation of the elongated member within the inner sleeve corresponds to a lengthening or shortening of the overall length of the connecting rod in the range of 0.1 mm to 5 mm per turn.

In some embodiments, the inner sleeve comprises a gradual adjustment indicator operable to indicate the relative configuration of the elongated member and the inner sleeve.

In some embodiments, the fastener comprises at least one of a tool manipulation facilitator and a manual manipulation facilitator.

In some embodiments, the fastener further comprises a fastener washer.

In some embodiments, the telescopic housing comprises one or more rapid adjustment indicators, and wherein the fastener washer comprises one or more indicators, such that the overall length of the connecting rod can be determined by comparing the one or more indicators of the fastener washer to the one or more rapid adjustment indicators of the telescopic housing.

In some embodiments, at least one of the telescopic housing, the inner sleeve, the first rotatable member housing, the second rotatable member housing, the first connecting member, or the second connecting member is comprised of stainless steel, hardened stainless steel, and/or titanium.

In some embodiments, the overall length of the connecting rod comprises a range of approximately 50 to 350 mm.

In some embodiments, the number of grooves defined in the wall of the at least one of the first and second joints comprises a range of three to five grooves.

In some embodiments, a method of maintaining the orientation of first and second rings for immobilizing bone segments may comprise providing a connecting rod comprising a telescopic housing comprising a proximal end, a distal end, and a first axial bore at least partially extending from the distal end to the proximal end, the first axial bore defining a first lengthwise axis; an inner sleeve slidably disposed within the first axial bore of the telescopic housing; a fastener operable to releasably couple the inner sleeve and the telescopic housing; an elongated member coupled to the inner sleeve; a first joint comprising a first rotatable member housing coupled to the proximal end of the telescopic housing; a first rotatable member disposed within the first rotatable member housing; and a first connecting member comprising a first connecting member insert coupled with the first rotatable member; wherein the first connecting member insert comprises a second axial bore defining a second lengthwise axis; and wherein the second axial bore is operable to receive a first connecting element from the first ring; and a second joint comprising a second rotatable member housing coupled to the elongated member; a second rotatable member disposed within the second rotatable member housing; and a second connecting member coupled with the second rotatable member, wherein the second connecting member is operable to couple with the second ring; and wherein at least one of the first and second joints comprises one or more grooves defined in the wall of the respective rotatable member housing, and the respective connecting member is disposed through one or more grooves, thereby limiting the rotation of the respective rotatable member in a first direction about the joint while allowing a greater range of motion in a second direction about the joint; and wherein the rotational movement of the first and second rotatable members is limited upon fixation of the respective connecting member to the respective ring; adjusting the longitudinal position of the inner sleeve relative to the telescopic housing about the first lengthwise axis; releasably coupling the inner sleeve to the telescopic housing using the fastener; releasably coupling the first connecting member to the first ring via the first connecting element disposed through the first ring, thereby limiting the rotational movement of the first rotatable member; and releasably coupling the second connection member to the second ring via a second connecting element, thereby limiting the rotational movement of the second rotatable member.

In some embodiments, the method may comprise gradually adjusting the length of the connecting rod after coupling of the first and second connecting members to the first and second rings, respectively, by rotating the elongated member relative to the inner sleeve about the first lengthwise axis.

BRIEF DESCRIPTION OF THE DRAWINGS

Some embodiments of the disclosure may be understood by referring, in part, to the present disclosure and the accompanying drawings, wherein.

DETAILED DESCRIPTION

The present disclosure includes embodiments directed to an external fixation connection rod with a housing that allows for rapid and/or gradual adjustment in length and having joint attachments to parallel or non-parallel rings or other external supports. Interfaces attaching the joints to external supports may provide advantages during connection rod attachment to and/or removal from external supports.

Figure 1A:
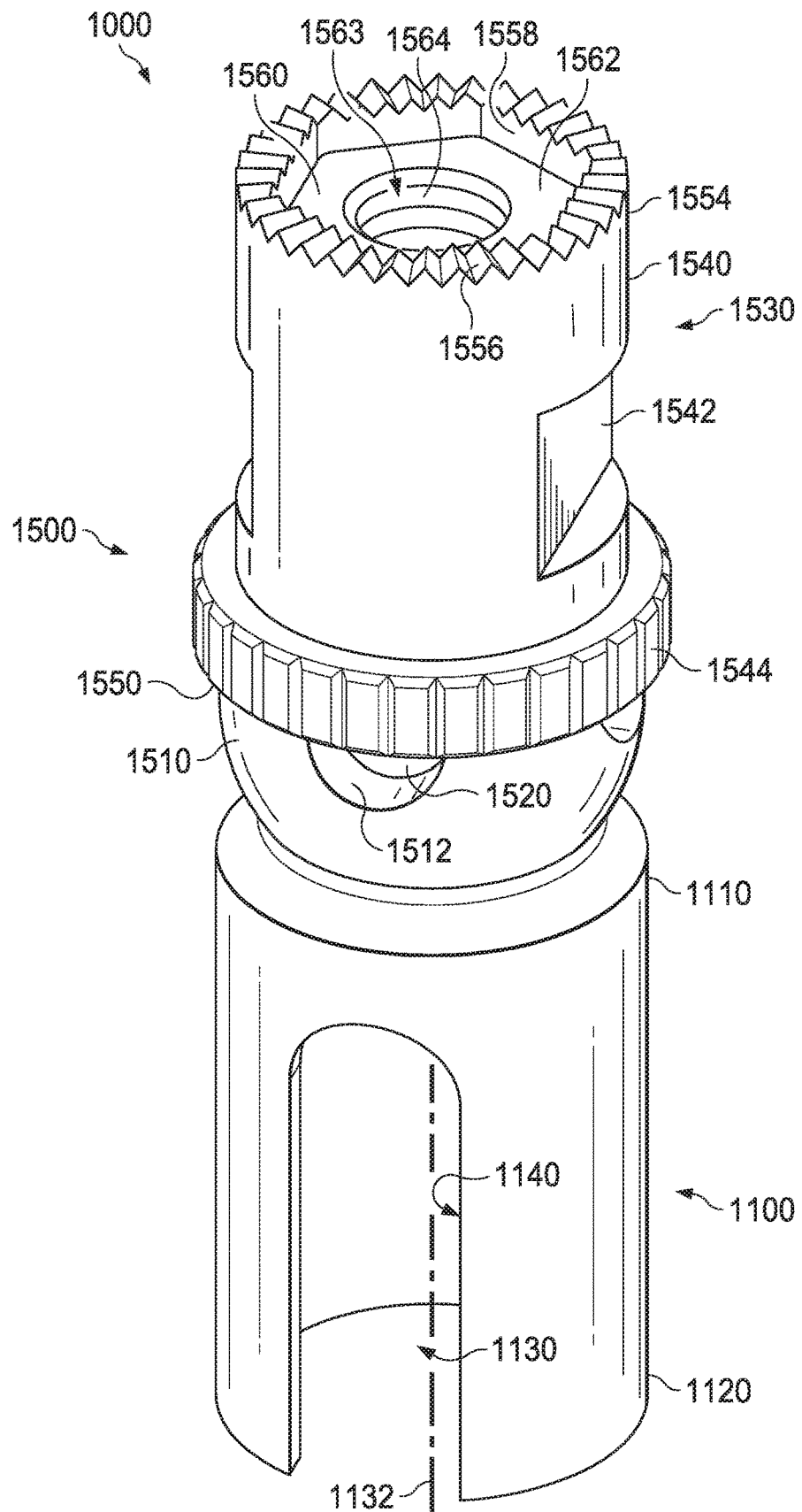
FIG. 1A illustrates a perspective view of a portion of a connecting rod according to a specific example embodiment of the disclosure.

FIG. 1A depicts a portion of a connecting rod 1000 according to an example embodiment of the present disclosure. The illustrated connecting rod 1000 portion may comprise a telescopic housing 1100, and a joint 1500 coupled with the telescopic housing 1100. The joint 1500 may be coupled with or comprise a connecting member 1530 operable to be coupled with a fixation ring (not shown in FIG. 1A).

The telescopic housing 1100 may comprise a proximal end 1110 and a distal end 1120. The distal end 1120 of the telescopic housing 1100 may extend further away from the proximal end 1110 (e.g., to provide a longer telescopic housing 1100) than what is illustrated in FIG. 1A. The telescopic housing 1100 may further comprise an axial bore 1130 extending from the distal end 1120 toward the proximal end 1110, e.g., in order to receive a slidable element (not shown in FIG. 1A) within the axial bore 1130. The axial bore 1130 may define a lengthwise axis 1132. The telescopic housing 1100 may also comprise an aperture 1140, which may facilitate translation motion of a fastener element (not shown in FIG. 1A) through the aperture 1140 and/or along the axial bore 1130.

The joint 1500 may comprise a rotatable member housing 1510 operable to contain a rotatable member 1520. Further, the rotatable member housing 1510 may comprise structural features (not fully shown in FIG. 1A) to limit the translational movement of the rotatable member 1520 with respect to the rotatable member housing 1510, e.g., so that the rotatable member 1520 stays within the rotatable member housing 1510. The rotatable member 1520 may also be referred to as a rotating member, and the rotatable member housing 1510 may also be referred to as a rotating member housing. The rotatable member housing 1510 may also comprise one or more grooves 1512 in the wall of the rotatable member housing 1510 to allow an attached connecting member 1530 to rotate more "deeply" into the directions of the grooves 1512 (i.e., rotate more off-axis relative to lengthwise axis 1132), and/or to limit rotation of the connecting member 1530 relative to lengthwise axis 1132 when the connecting member 1530 is rotated into one of the grooves 1512. Note that grooves 1512 may also be referred to as recesses, slots, and/or channels. The one or more grooves 1512 may advantageously provide the connecting member 1530 a wider range of rotational motion (e.g., during external fixation ring installation and/or de-installation) while still providing structural containment of the rotatable member 1520 and/or "locking" the rotational position of the connecting member 1530 in place with respect to lengthwise axis 1132 after installation into an external fixation ring in order to prevent undesired movement of the connecting rod 1000.

The joint 1500 may further comprise or be connected to a connecting member 1530. The connecting member 1530 may comprise a stem (not shown in FIG. 1A) that couples with the rotatable member 1520, at least a portion of which is operable to be disposed within at least a portion of the one or more grooves 1512, in order to facilitate the functions of the one or more grooves 1512 (i.e., increase rotational depth and/or limit rotational movement of the connecting member 1530). The connecting member 1530 may further comprise a connecting member insert 1560 and a connecting member housing 1540. The connecting member housing 1540 may also be referred to as a seating member, given that a coupling end 1554 of the connecting member housing 1540 may provide a "seat" for an external fixation ring to rest upon during and after installation.

The connecting member housing 1540 may comprise a coupling facilitator 1556 on the coupling end 1554 in order to stabilize mechanical contact between the connecting member 1530 and an external fixation ring. In some embodiments the coupling facilitator 1556 may comprise ridges and/or a roughened surface, e.g., in order to increase the friction of mechanical contact, and/or to provide structural impediments to rotational motion of the connecting member 1530 across the surface of an external fixation ring. In some embodiments, an external fixation ring may comprise a complementary coupling surface in order to mate with the coupling facilitator 1556 of the connecting member 1530. The coupling surface of an external fixation ring may or may not be roughened in order to increase friction between the connecting member 1530 and the external fixation ring.

The connecting member insert 1560 may comprise an axial bore 1563 with internal threads 1564, e.g., for receiving a threaded connecting element (not shown in FIG. 1A) in order to connect the connecting member 1530 to an external fixation ring. The axial bore 1563 may also be referred to as a connecting member insert cavity. The connecting member insert 1560 may be rigidly (or at least rotationally) coupled to the rotatable member 1520 via a stem (not shown in FIG. 1A). The connecting member insert 1560 may further comprise a non-circular head 1562, and the connecting member housing 1540 may comprise a non-circular cavity 1558, such that the connecting member insert 1560 cannot rotate with respect to the connecting member housing 1540. This "rotational coupling" of the connecting member insert 1560 and connecting member housing 1540 may advantageously allow for the connecting member insert 1560 to be separate from the connecting member housing 1540 (e.g., for manufacturing and/or assembly purposes) while allowing the connecting member to be indirectly rotated (e.g., for tightening the connecting member insert 1560 with respect to an external fixation ring) by rotating the connecting member housing 1540. The connecting member housing 1540 may comprise a tool manipulation facilitator 1542 (e.g., tool mating depressions) operable to allow a tool (e.g., a wrench) to rotate the connecting member housing 1540, and/or a manual manipulation facilitator 1544 (e.g., a ridged surface) operable to allow a human hand to rotate the connecting member housing 1540. While the tool manipulation facilitator 1542 and the manual manipulation facilitator 1544 are illustrated in FIG. 1A between the coupling end 1554 and the base 1550 of the connecting member housing 1540, and near the base 1550, respectively, it will be understood that the tool manipulation facilitator 1542 and manual manipulation facilitator 1544 may be located anywhere along the outside wall of the connecting member housing 1540.

A potential further advantage of the separation of the connecting member insert 1560 from the connecting member housing 1540 is the ability to inhibit joint 1500 (and therefore connecting member 1530) rotation after tightening the connecting member 1530 against an external fixation ring, as will be described. During installation of the connecting member 1530 to an external fixation ring, the mechanical coupling between the connecting member insert 1560 and the rotatable member 1520 (e.g., via the stem) results in both the connecting member insert 1560 and the rotatable member 1520 being pulled toward an external fixation ring along a lengthwise axis defined by the axial bore 1563 of the connecting member insert 1560. In other words, the connecting member insert 1560 can slide axially within the connecting member housing 1540, thus tightening or loosening the friction fit between the rotatable member 1520 and the rotatable member housing 1510. The connecting member insert 1560 will continue to be pulled toward the external fixation ring, e.g., due to the screwing of a connecting element (e.g., a threaded bolt) inserted through the external fixation ring and into an internally-threaded axial bore 1563 of the connecting member insert 1560, until either the head 1562 of the connecting member insert 1560 or some intervening structure (e.g., the coupling end 1554 of the connecting member housing 1540) makes physical contact with the coupling surface (not shown in FIG. 1A) of the external fixation ring. Assuming the connecting member housing 1540 spans a sufficiently long distance from its base 1550 to its coupling end 1554, and assuming that the connecting member insert 1560 is sufficiently recessed within the rotatable member housing 1510, such that the head 1562 of the connecting member insert 1560 cannot be pulled beyond the coupling end 1554 of the connecting member housing, a "simultaneous tightening" will occur. In particular, the rotatable member 1520 will be pulled proximally (i.e., in a direction generally away from the telescopic housing 1100) against the inside of the rotatable member housing 1510, which will in turn pull a proximal portion of the outside of the rotatable member housing 1510 against the connecting member housing 1540, thereby compressing the connecting member housing 1540 between the rotatable member housing 1510 and the external fixation ring. As a result, the rotatable member housing 1510 will be compressed against both the rotatable member 1520 and the connecting member housing 1540 to form a secure frictional fit, thus substantially if not completely inhibiting rotation of the joint 1500 after tightening of the connecting member 1530 to the external fixation ring.

A connecting member 1530 of the embodiment shown in FIG. 1A may also be referred to as a receiving member or a female connecting member due to the ability of the illustrated connecting member 1530 to receive a connecting element, e.g., a screw (not shown in FIG. 1A), and/or due to a lack of physical structure protruding beyond the coupling end 1554 of the connecting member housing 1540. Further, a joint 1500 coupled with a female connecting member may be referred to as a female joint and/or a female attachment. A receiving member may be advantageous (e.g., as opposed to a connecting member with physical structure, such as a screw, protruding beyond the coupling end 1554) because upon insertion and/or removal of a connecting element connecting the receiving member to an external fixation ring, the receiving member can be installed and/or removed from the external fixation ring in a direction not necessarily aligned with the insertion axis of the connecting element (e.g., threaded bolt or screw). In other words, a receiving member can be translated along and off the coupling surface of the external fixation ring, without the separation necessarily occurring along the axis of connecting element insertion, as would be the case for a non-receiving connecting member (e.g., a "male connecting member").

Figure 1B:
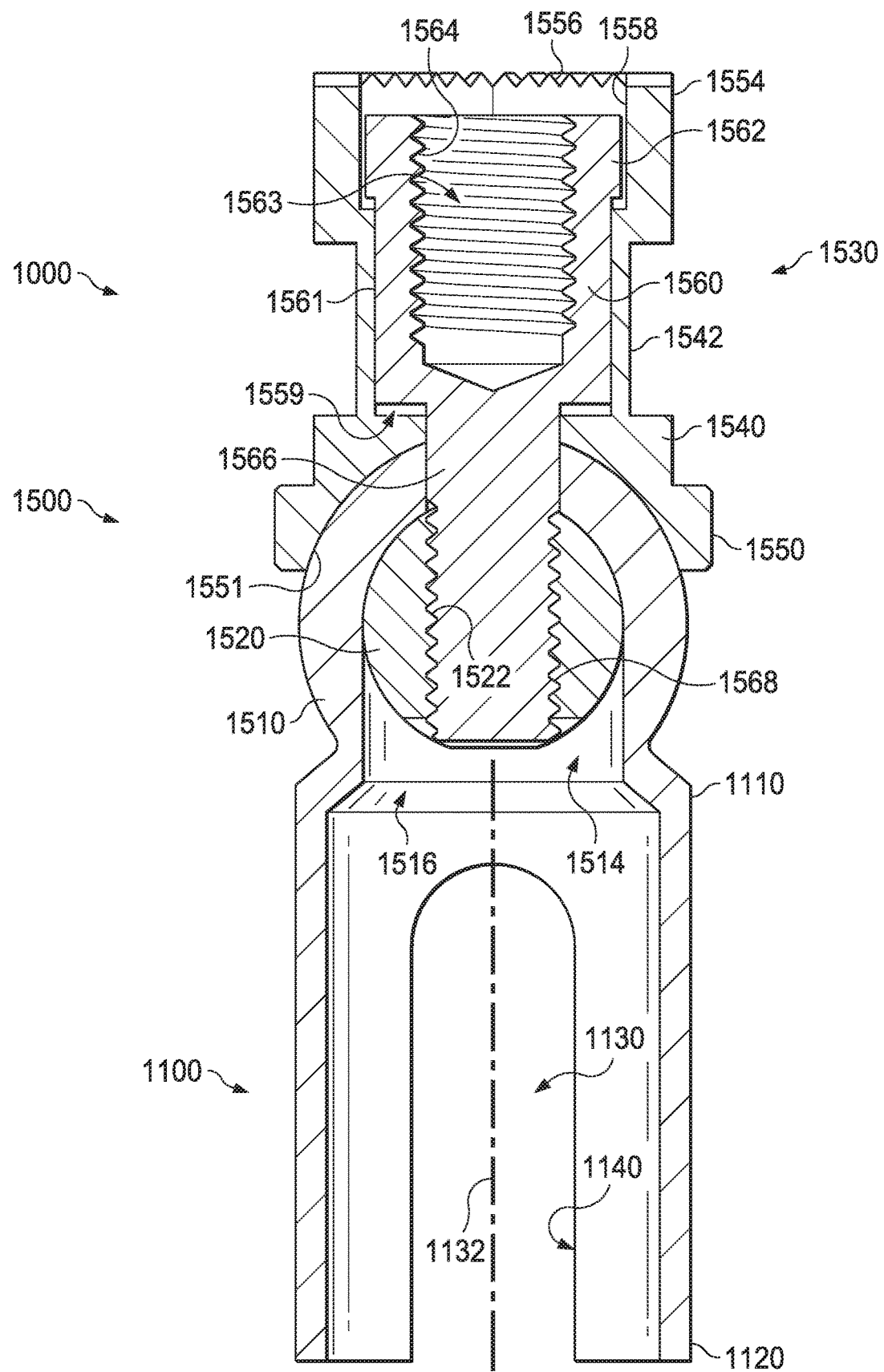
FIG. 1B illustrates a cross-sectional view of a portion of a connecting rod according to a specific example embodiment of the disclosure.

FIG. 1B depicts a cross section of the connecting rod 1000 of FIG. 1A. As is illustrated, the rotatable member 1520 is contained in the rotatable member housing 1510 despite grooves and/or other openings in the rotatable member housing 1510 via structure extending over the rotatable member 1520. During assembly, the rotatable member 1520 can be inserted through an aperture 1516 in the rotatable member housing 1510 into a cavity 1514 allowing rotation of the rotatable member 1520. As also shown in FIG. 1B, the connecting member insert 1560 may be integrally formed with or coupled to a stem 1566, which in turn may be integrally formed with or coupled (e.g., threadably) to the rotatable member 1520. Therefore, the base of the connecting member insert 1560 may comprise external threads 1568 operable to mate with internal threads 1522 of the rotatable member 1520. The coupling between the rotatable member 1520 and the connecting member insert 1560 is operable to prevent the rotatable member 1520 from falling out through the aperture 1516 once assembled.

Further, as is illustrated in FIG. 1B, an inner recessed portion 1551 near the base 1550 of the connecting member housing 1540 is formed (e.g., complementarily) to allow for rotational motion of the connecting member housing 1540 over the rotatable member housing 1510 during joint configuration while still providing a relatively large frictional surface for purposes of joint 1500 rotation inhibition after installation of the connecting member 1530 to an external fixation ring, as described with respect to FIG. 1A.

It is further illustrated that the connecting member insert 1560 may comprise a circular portion 1561 disposed in a circular cavity 1559 of the connecting member housing 1540, which does not "rotationally couple" the connecting member insert 1560 and the connecting member housing 1540. The circular portion 1561 and circular cavity 1559 are optional (i.e., the connecting member insert 1560 may only comprise a non-circular head 1562, and the connecting member housing 1540 may only comprise a non-circular cavity 1558), but may reduce manufacturing costs and/or reduce the overall size of the connecting member 1530. Further it will be understood that the non-circular head 1562 portion of the connecting member insert 1560 need not be position at the proximal end of the connecting member insert 1560, e.g., the location of the non-circular head 1562 and the circular portion 1561 along the length of connecting member insert 1560 could be reversed or even intermixed.

Finally, as described with respect to FIG. 1A, the structure of the connecting member insert 1560 in relation to the connecting member housing 1540 may advantageously be such that the proximal end (as presently illustrated, the non-circular head 1562) of the connecting member insert 1560 cannot be pulled beyond the coupling end 1554 of the connecting member housing 1540 during an installation tightening procedure, which compresses the rotatable member housing 1510 between the pulled rotatable member 1520 and the compressed connecting member housing 1540, thereby resulting in an overall inhibition of joint 1500 rotation. As illustrated, there may exist some play (i.e., gaps) between the connecting member insert 1560 and the connecting member housing 1540 during a tightened state and/or during and untightened state. The gaps may exist to prevent "seizing" of the connecting member 1530 relative to the joint 1500, but would not generally preclude the tightening advantages during coupling with an external fixation ring as described above.

Figure 2A:
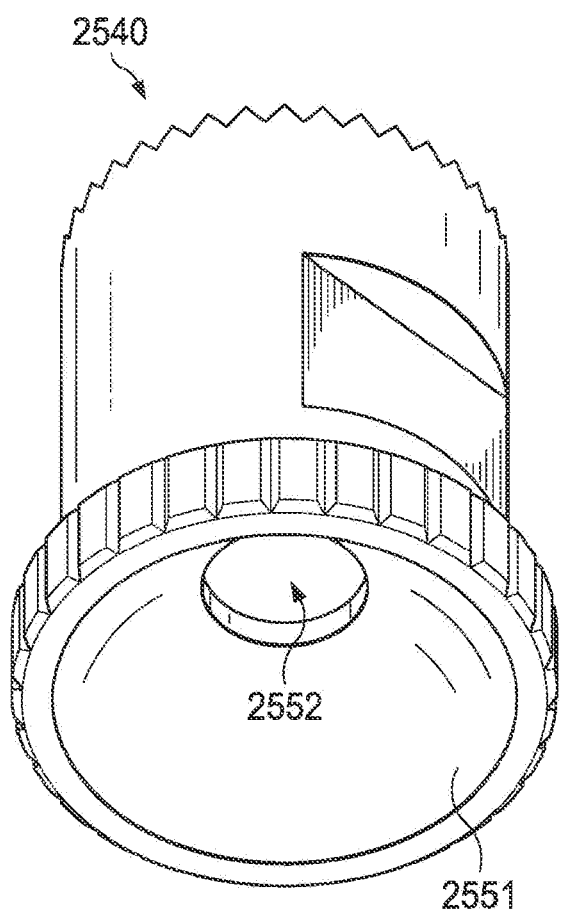
FIG. 2A illustrates a perspective view of a portion of a connecting member according to a specific example embodiment of the disclosure.
Figure 2B:
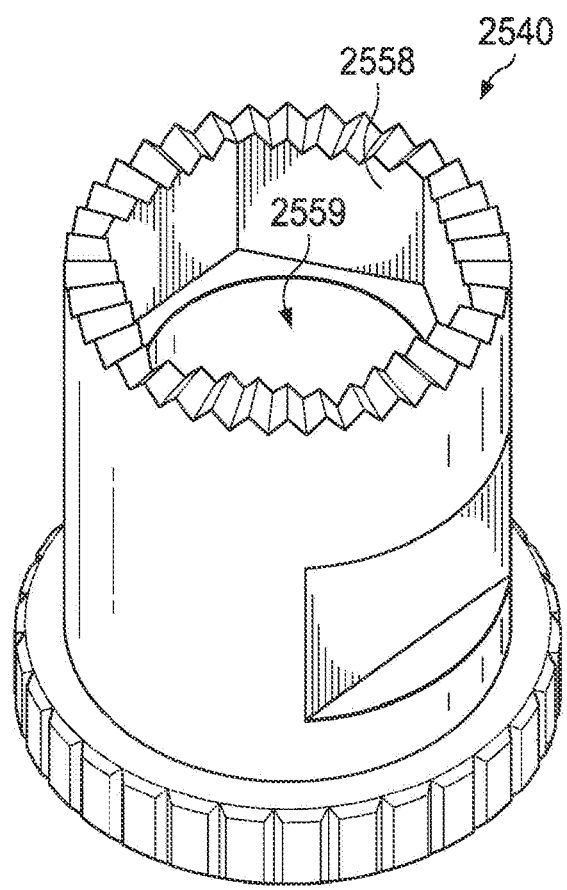
FIG. 2B illustrates a perspective view of a portion of a connecting member according to a specific example embodiment of the disclosure.
Figure 2C:
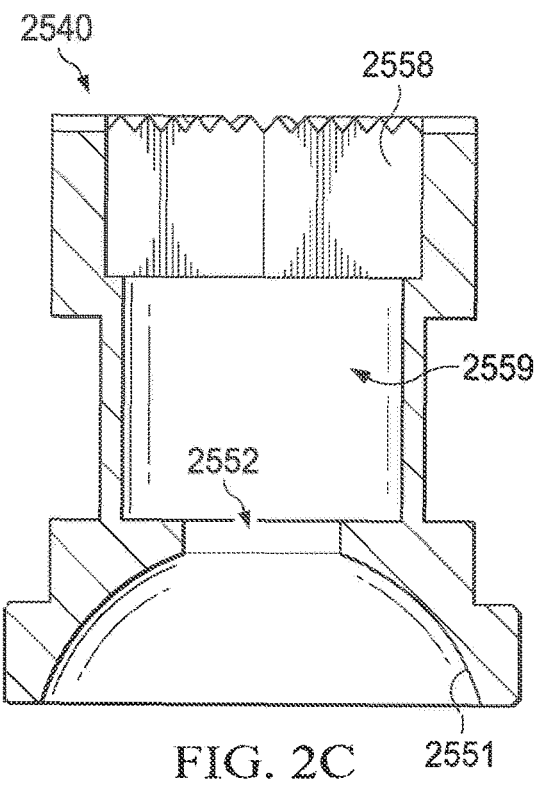
FIG. 2C illustrates a cross-sectional view of a portion of a connecting member according to a specific example embodiment of the disclosure.

FIGS. 2A, 2B, and 2C depict perspective views of an example embodiment of a connecting member housing 2540, which may form a portion of a connecting member. As illustrated in FIGS. 2A and 2C, the inner recessed portion 2551 of the connecting member housing 2540 may comprise a spherical profile, e.g., to complement the outer contour of an rotatable member housing (not shown in FIGS. 2A-2C). Further, as illustrated in FIGS. 2A and 2C, the connecting member housing 2540 may comprise an aperture 2552 large enough to allow a portion of a connecting member insert (not shown in FIGS. 2A-2C), e.g., the stem, to pass through, but small enough to prevent another portion, i.e., a portion with a larger radius such a non-circular head and/or circular portion, from passing through. Similar to the non-circular cavity 2558, the circular cavity 2559 provides a region to contain and align a portion of a connecting member insert within the connecting member housing 2540 about an axis corresponding to an axial bore of the connecting member insert (not shown in FIGS. 2A-2C), while also allowing axial translation of the connecting member housing along the axis corresponding to the axial bore of the connecting member insert. As illustrated in FIGS. 2B and 2C, the circular cavity 2559 of the connecting member housing 2540 may have a smaller radius than the non-circular cavity 2558.

Figure 3A:
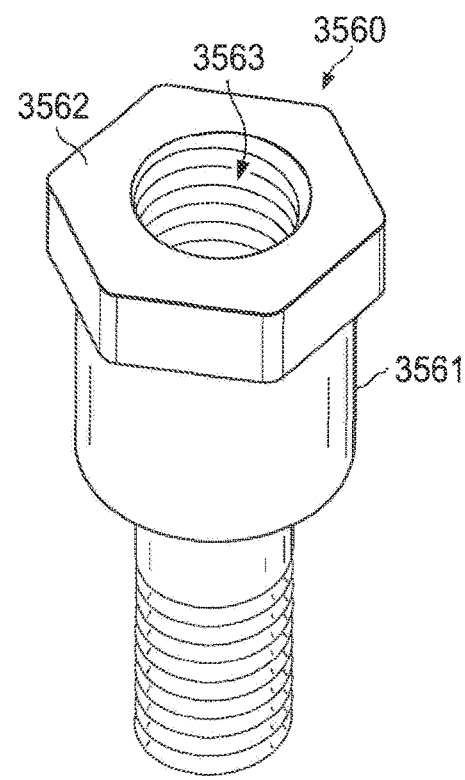
FIG. 3A illustrates a perspective view of a portion of a connecting member according to a specific example embodiment of the disclosure.
Figure 3B:
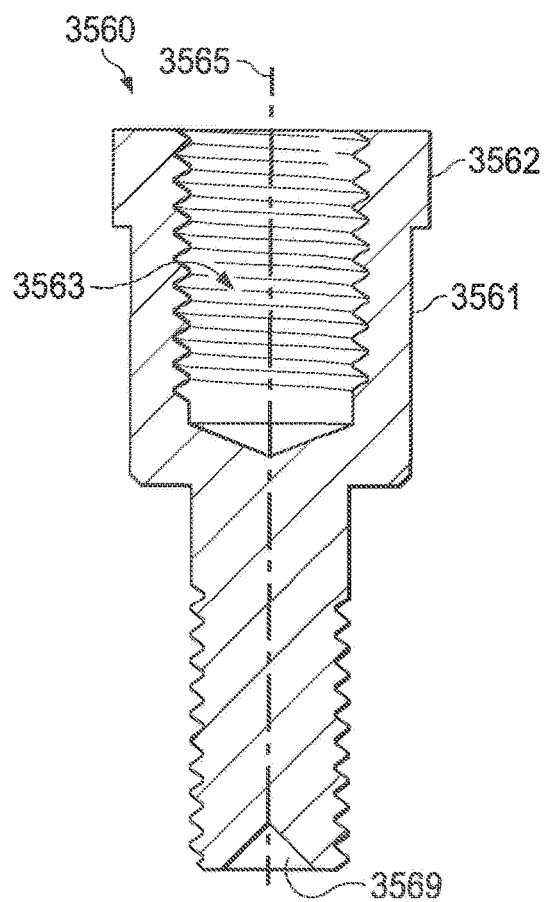
FIG. 3B illustrates a cross-sectional view of a portion of a connecting member according to a specific example embodiment of the disclosure.
Figure 3C:
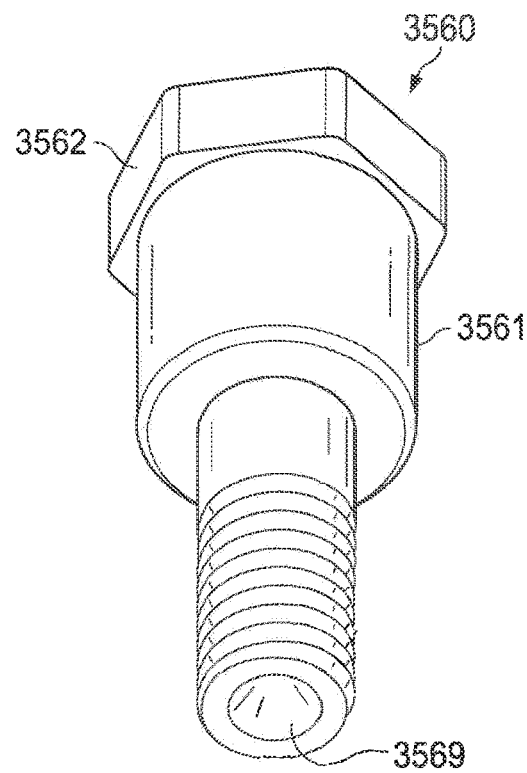
FIG. 3C illustrates a perspective view of a portion of a connecting member according to a specific example embodiment of the disclosure.

FIGS. 3A, 3B, and 3C depict perspective and cross-sectional views of an example embodiment of a connecting member insert 3560. As previously noted, the non-circular head 3562 portion may be formed at a different location along the connecting member insert 3560 (e.g., the non-circular head 3562 may be positioned in the place of the circular portion 3561, and vice versa). Therefore, it is not necessary that the non-circular head 3562 portion have a larger radius than the circular portion 3561 while still creating a rotational coupling between the connecting member housing (not shown in FIGS. 3A-3C) and the connecting member insert 3560. For example, the circular cavity and non-circular cavity of the connecting member housing may be similarly rearranged both in position and radius to accommodate a corresponding connecting member insert.

The axial bore 3563 of the connecting member insert 3560 defines a lengthwise axis 3565 about which a connecting member housing may be rotationally coupled to the connecting member insert 3563, about which a rotatable member can be rotated within a rotatable member housing (not shown in FIGS. 3A-3C), and about which a connecting member comprising the connecting member insert 3563 can be rotated during an installation and/or tightening procedure with respect to an external fixation ring.

The connecting member insert 3560 may comprise one or more depressions on an end opposite the end of a non-circular head 3562. The geometry of the one or more depressions may depend on the method of manufacturing. For instance, use of a drill bit may form a spherical or conical depression (as shown), while use of a 90° tipped-end mill may form a flat end and/or depression. The one or more depressions 3569 may be advantageous, e.g., by allowing a tool used for joint assembly on a proximal end of a telescopic housing to at least partially enter the one or more depressions during assembly. As another example of a possible advantage, a rotatable member (not shown in FIGS. 3A, 3B, or 3C) may comprise tabs that can be folded into one or depressions of the connecting member insert 3560 (e.g., for more compact final assembly and/or for a rotational "locking" of the rotatable member with respect to the connecting member insert 3560). The one or more depressions may be a side effect of and/or facilitate manufacturing of the connecting member insert 3560.

Figure 4:
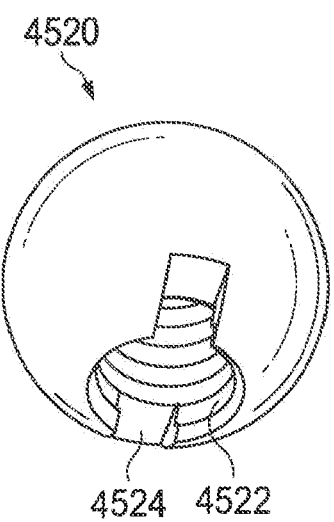
FIG. 4 illustrates a perspective view of a portion of a joint according to a specific example embodiment of the disclosure.

FIG. 4 depicts a perspective view of an example embodiment of a rotatable member 4520. The rotatable member 4520 may comprise a spherical profile, as illustrated. Note that the threads 4522 need not extend all the way through the rotatable member 4520, but doing so may be beneficial, e.g., for manufacturing purposes and/or for more permanent coupling with a connecting member insert. Additionally, while the tool manipulation facilitator 4524 as illustrated here comprises depressions into the rotatable member, it will be understood that other structure features (e.g., protruding hooks or knobs) may similarly achieve the purpose of holding the rotatable member 4520 in place during assembly, while not deleteriously affecting the rotation of the rotatable member 4520 within a rotatable member housing during operation.

Figure 5:
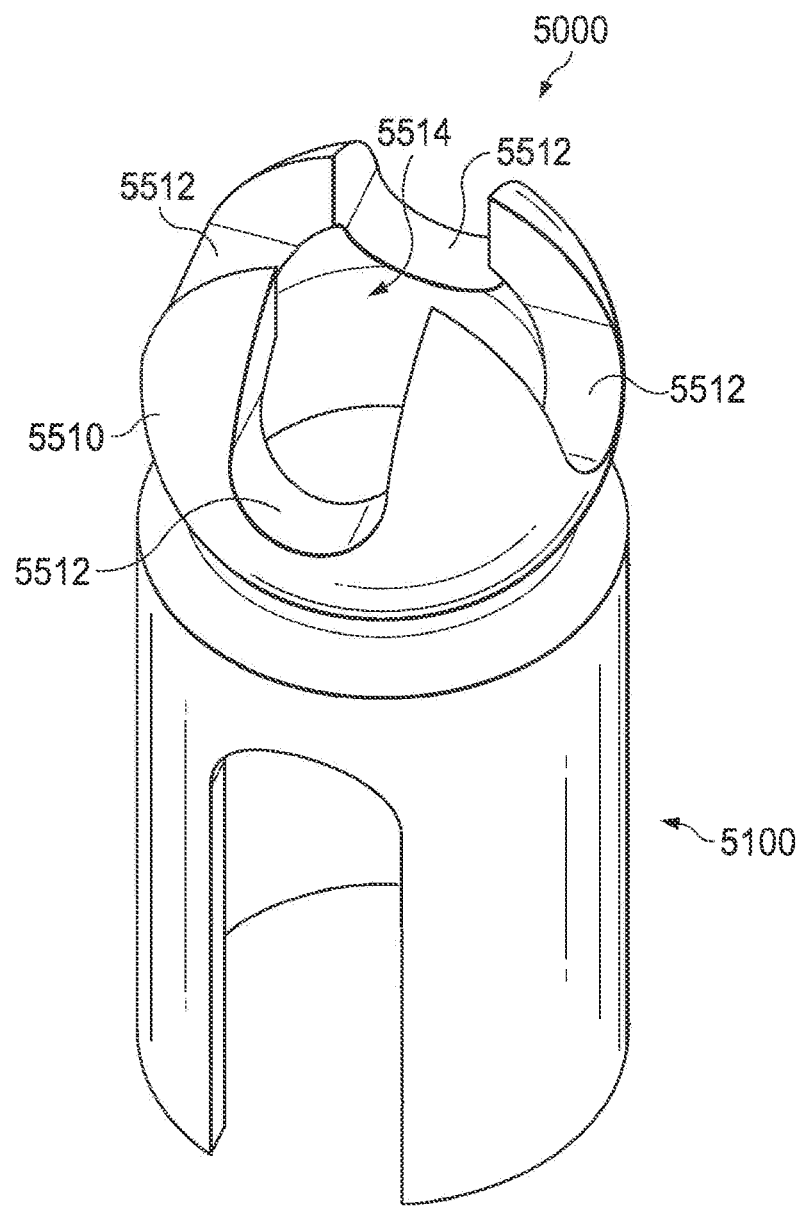
FIG. 5 illustrates a perspective view of a portion of a connecting rod according to a specific example embodiment of the disclosure.

FIG. 5 illustrates an example embodiment of a connecting rod portion 5000. Grooves 5512 may be symmetrically positioned across rotatable member housing 5510 to form "cross-channels" operable to guide the off-axis pivoting of a connecting member (not shown in FIG. 5) with respect to a lengthwise axis defined by the telescopic housing 5100.

However, grooves 5512 need not be symmetrically aligned. Additionally, grooves need not be "straight", but may form curved paths within the rotatable member housing 5510 side walls, which may provide alternative range of motion and/or connecting member "locking" characteristics after installation. In general, grooves 5512 may provide a connecting member additional range of motion while still leaving enough rotatable member housing 5510 side wall structure to contain a rotatable member (not shown in FIG. 5). Additionally, grooves 5512 may provide structural impediments to rotation of a connecting member about a lengthwise axis defined by the telescopic housing 5100 after insertion of a stem of the connecting member into a groove 5512. In some embodiments, three to five (e.g., four) grooves 5512 may be formed in the sidewall of the rotatable member housing 5510. An odd number of grooves 5512 (e.g., three) may comprise zero or more cross-channels.

It will also be understood that the cavity 5514 of the rotatable member housing 5510 may or may not be formed complementarily to a rotatable member (e.g., may form a non-spherical shape with sufficiently large radius to allow full rotation of a rotatable member), and may or may not provide "play" (i.e., air gaps) for a rotatable member disposed therein (e.g., to prevent seizing and/or account for manufacturing tolerances).

Figure 6:
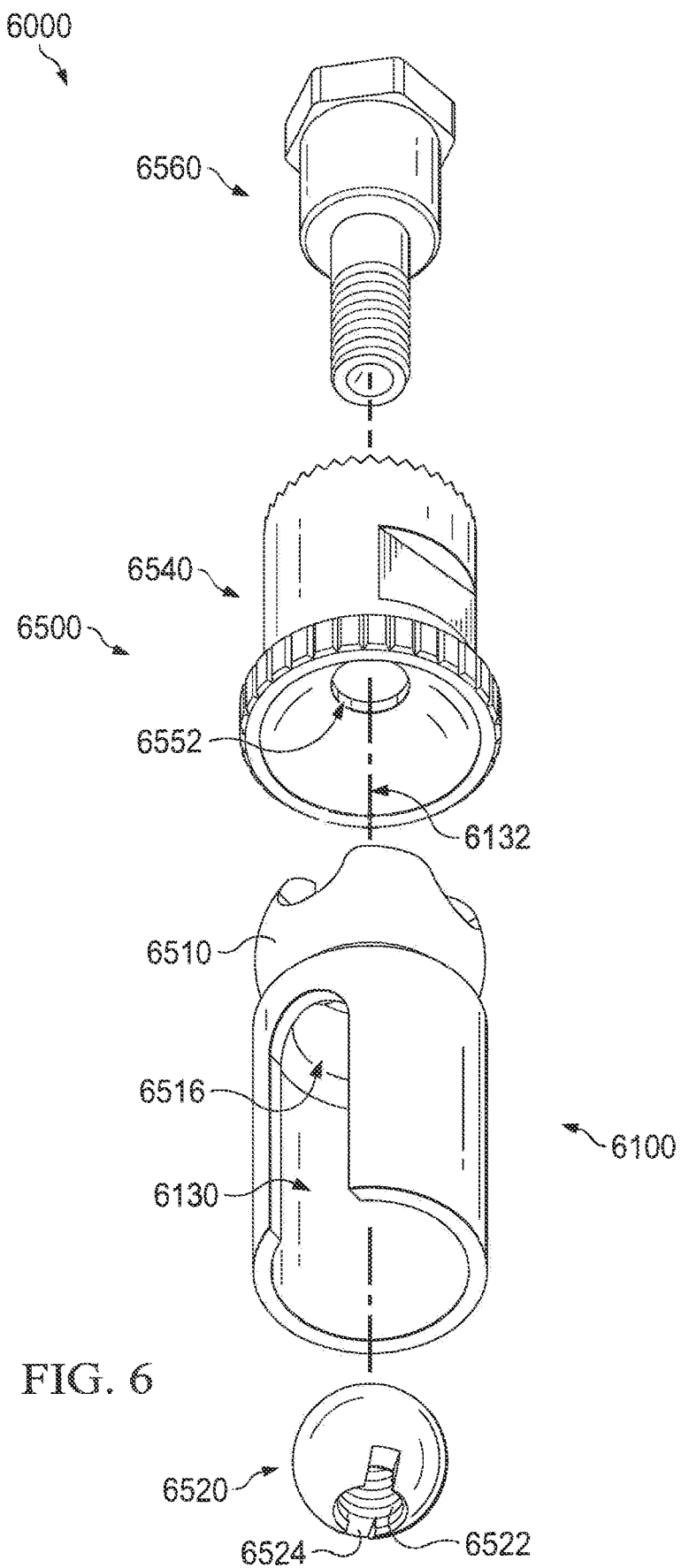
FIG. 6 illustrates an exploded view of a portion of a connecting rod according to a specific example embodiment of the disclosure.

FIG. 6 depicts an exploded view of an example embodiment of a connecting rod portion 6000. During assembly, the rotatable member 6520 can be inserted through the axial bore 6130 of the telescopic housing 6100, through an aperture 6516 in a proximal portion of the rotatable member housing 6510, and into a cavity (not labeled in FIG. 6). Further, the rotatable member 6520 can be rotationally fixed during coupling with a connecting member insert 6560 via a tool manipulation facilitator 6524 of the rotatable member 6520. For example, as illustrated the tool manipulation facilitator 6524 may comprise depressed slots operable to mate with tools such as a flathead (also "slotted", or "standard") screwdriver, needle nose pliers, or a similarly effective tool.

The connecting member insert 6560 may be inserted through an aperture 6552 of the connecting member housing 6540 and through an opening in the rotatable member housing 6510, in order to couple (e.g., threadably, as illustrated) with the rotatable member 6520. It will be understood that an internally threaded 6522 bore of the rotatable member need not extend through the entire rotatable member.

After coupling, the rotatable member 6520 is restrained from falling through the aperture 6516, at least until an intentional disassembly of the joint 6500 is performed. Further, after assembly, the rotatable member 6520 and the connecting member insert 6560 become a single rotationally-coupled rigid body, both with respect to a "twisting" rotation relative to a lengthwise axis defined by the axial bore (not shown in FIG. 6) of the connecting member insert 6560, and with respect to an off-axis "pivoting" rotation of the connecting member insert 6560 relative to the lengthwise axis 6132 defined by the telescopic housing 6100. A lengthwise axis may also be referred to as a longitudinal axis.

Figure 7A:
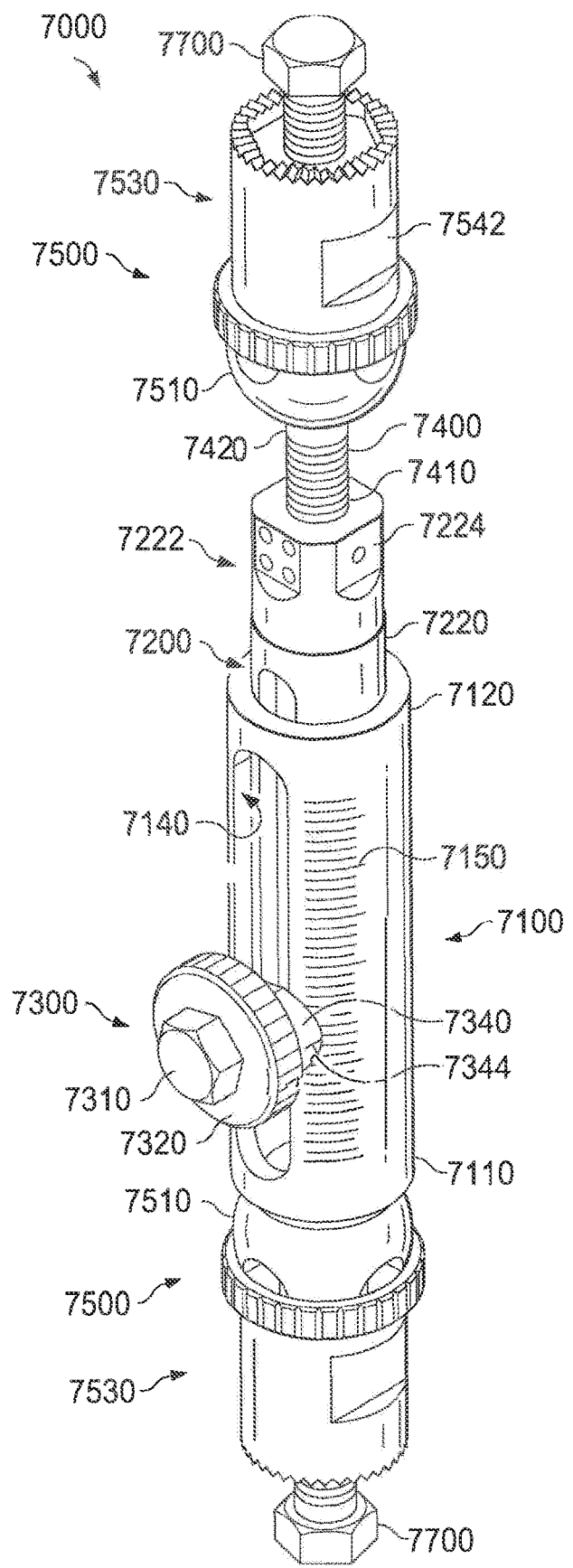
FIG. 7A illustrates a perspective view of a connecting rod according to a specific example embodiment of the disclosure.
Figure 7B:
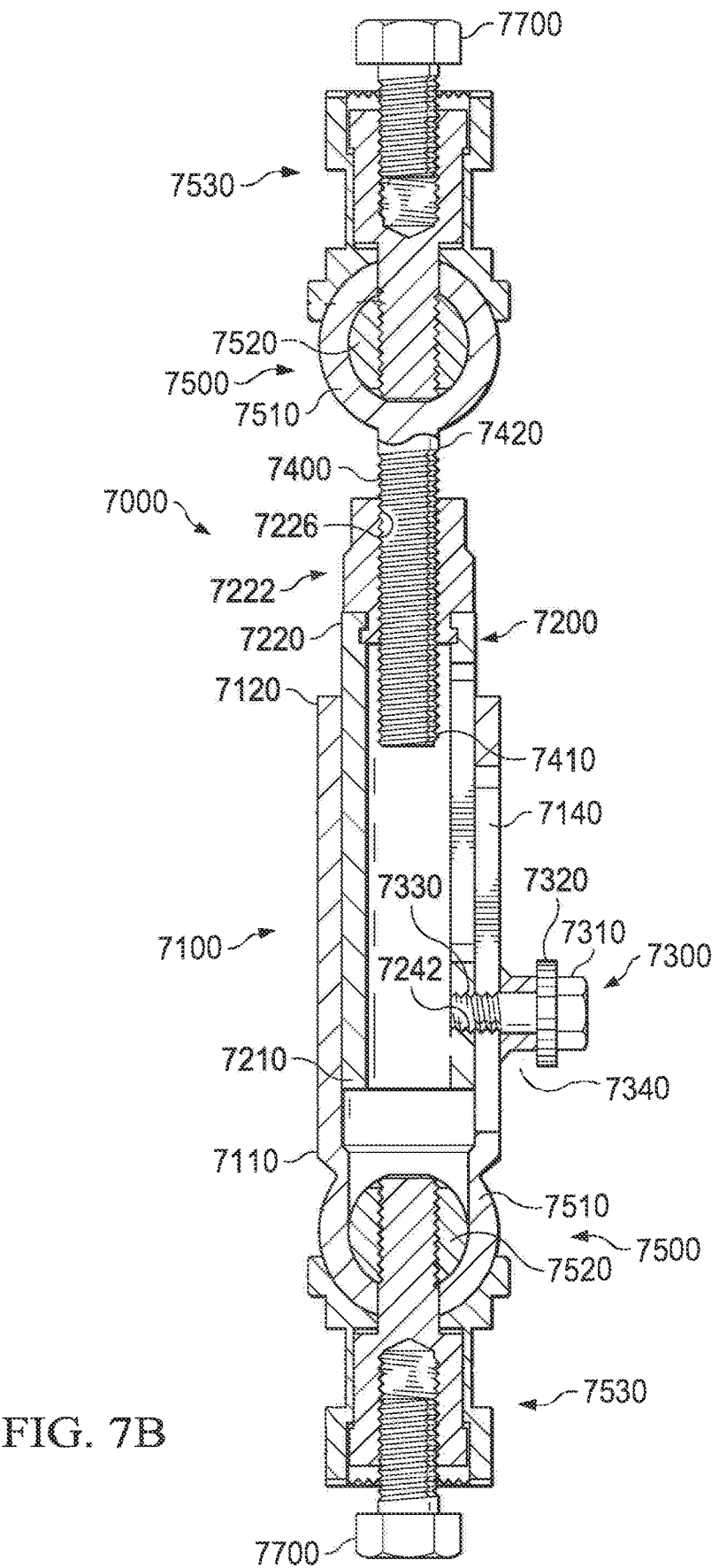
FIG. 7B illustrates a cross-sectional view of a connecting rod according to a specific example embodiment of the disclosure.

FIGS. 7A and 7B depict a perspective and cross-sectional view of an example embodiment of a connecting rod 7000. A telescopic housing 7100 may comprise a proximal end 7110 and a distal end 7120. A proximal female joint 7500 (also may be referred to as a "female attachment"), as previously described, may be coupled to the proximal end 7110 of the telescopic housing 7100. An inner sleeve 7200 may be slidably disposed within the telescopic housing 7100, e.g., after assembly of the proximal joint 7500, after insertion of a proximal end 7210 of the inner sleeve 7200 through the distal end 7120 of the telescopic housing 7100. Further, a fastener 7300 may be operable to releasably couple the inner sleeve 7200 to the telescopic housing 7100. An inner sleeve may also be referred to as an adjustment sleeve. A gradual adjustment mechanism 7222 may be coupled to or comprised in the distal end 7220 of the inner sleeve 7200. An elongated member 7400 may couple with the gradual adjustment mechanism 7222 and may further couple with a distal joint 7500. The distal joint 7500 may couple to a female connecting member 7530 (as illustrated), or may couple to a "male" connecting member (not shown). Female connecting members 7530 may further couple to a connecting element 7700, e.g., a threaded bolt (as illustrated), during coupling to an external fixation ring (not shown in FIGS. 7A and 7B). A connecting element may also be referred to as a ring fastener. A connecting element may be separate from or integrally formed with an external fixation ring.

A fastener 7300 may comprise a tool manipulation facilitator 7310 (e.g., a bolt head for mating with a wrench, as illustrated), a manual manipulation facilitator 7320 (e.g., a textured surface operable to be twisted by a human hand, as illustrated), a coupling mechanism 7330 (e.g., external threads, as illustrated), and an intermediate component 7340 (e.g., a washer, as illustrated). The fastener 7300 may extend through the aperture 7140 of the telescopic housing 7100, and at least partially into the inner sleeve 7200. For example, as illustrated in FIG. 7B, the fastener 7300 extends partially into and threadably couples with the inner sleeve 7200, thereby creating a friction fit between the inner sleeve 7200 and the telescopic housing 7100 when the fastener 7300 is tightened against the inner sleeve 7200, thus compressing the telescopic housing 7100 between the inner sleeve 7200 and the fastener, forming a rigid friction fit. The intermediate component 7340, though optional, may facilitate the friction fit by creating a larger frictional surface between the fastener 7300 and the telescopic housing 7100. For example, as illustrated, a washer 7340 is formed to complement the curved outer surface of the telescopic housing 7100 and the flat under surface of the manual manipulation facilitator 7320 of the fastener 7300. The inner sleeve 7200 may have structure mating features (e.g., internal threads 7242) to couple with the fastener 7300. It will be understood that other structural embodiments could also accomplish releasably coupling the telescopic housing 7100 and the inner sleeve 7200.

The fastener 7300 may provide "rapid adjustment" functionality by allowing an operator to slidably position the inner sleeve 7200 with respect to the telescopic housing 7100, when the fastener is loosened, and then tighten the fastener once a desired position is reached. Because there connecting rod 7000 also comprises a gradual adjustment mechanism 7222, the rapid adjustment may only be a coarse positioning that is further refined. The fastener 7300 and the telescopic housing 7100 may comprise rapid adjustment indicators 7344, 7150 in order to quantify and/or create reproducibility of the rapid adjustment length.

The inner sleeve 7200 may comprise or may be coupled to a gradual adjustment mechanism 7222 that provides for a slower, but finer-resolution adjustment of the connecting rod 7000 length. As illustrated in FIG. 7B, the gradual adjustment mechanism 7222 may comprise an axial bore with internal threads 7226 for translatably coupling with the (e.g., externally threaded, as illustrated) elongated member 7400. A proximal end 7410 of the elongated member 7400 may be inserted through the gradual adjustment mechanism 7222, after which a "twisting" rotation of the elongated member 7400 with respect to the gradual adjustment mechanism 7222 (by hand or tool) may be operable to increase or decrease the length of the connecting rod 7000. The gradual adjustment mechanism 7222 may or may not be twistably rotatable relative to the inner sleeve 7200. Some embodiments may not comprise a gradual adjustment mechanism 7222 (for example, lack of a gradual adjustment mechanism 7222 may be desirable in order to increase stability, e.g., in trauma applications).

It will be understood that the general operation of the gradual adjustment mechanism 7222 is to translatably lengthen or shorten the overall length of the connecting rod 7000. Therefore, other embodiments, such as elongated member 7400 coupled to a gradual adjustment mechanism 7222 comprising an axial bore with internal threads operable to twistably rotate with respect to an externally threaded distal end 7120 of an inner sleeve, may be envisioned.

The gradual adjustment mechanism 7222 may comprise a gradual adjustment indicator portion 7224, which may also double as a tool and/or manual manipulation facilitator for twisting the gradual adjustment mechanism 7222 with respect to the elongated member 7400. The gradual adjustment indicator portion 7224 may provide for relative quantification and/or reproducibility of the connecting rod 7000 length. For example, a patient or medical professional may be instructed to adjust the gradual adjustment mechanism 7222 according to some treatment regime. Further, the gradual adjustment indicator portion 7224 may comprise one or more sides with indicators depending on the desired granularity of length adjustment. For example, FIG. 7A depicts a four-sided indicator portion 7224. In some embodiments a full (i.e., 360-degree) turn of the gradual adjustment mechanism 7222 with respect to the elongated member 7400 may produce 0.1-5.0 mm (e.g., 1.0 mm) of translational adjustment.

The relative position of the elongated member 7400 with respect to the gradual adjustment mechanism 7222 may be stable during use of the connecting rod 7000 due to a twisting resistance between the elongated member 7400 and the gradual adjustment mechanism 7222. The twisting resistance may come about due to a threadable coupling and/or due to compressive pressure from two attached external fixation rings (not shown in FIGS. 7A and 7B).

Integrally formed with or coupled to a distal end 7420 of the elongated member is a distal joint 7500. The distal joint 7500 may comprise identical structure (as illustrated) as that of the proximal joint 7500, or may comprise alternative structure (e.g., a "male connecting member"), e.g., as illustrated and described in U.S. Pat. No. 9,456,849. It may be advantageous to have a "male" connecting member (or attachment) on one end of the connecting rod, e.g., for geometry (e.g., lower profile), manufacturing (e.g., less materials), and/or assembly (e.g., fewer assembly steps and/or easier assembly) purposes.

In order to assemble the distal joint 7500, the sidewall structure of the rotatable member housing 7510 containing the rotatable member 7520 may be manufactured in an "open" configuration (e.g., sidewall structure next to grooves "straight up", not curved) such that the rotatable member 7520 can be inserted from the distal end, and "closed" (e.g., by bending the rotatable member housing 7510 over the rotatable member 7520) after insertion of the rotatable member 7520. Alternatively, the rotatable member housing 7510 of the distal joint 7500 may not be integrally formed with the elongated member 7400, such that an aperture (not shown) allows for insertion of the rotatable member 7520, after which the distal joint 7500 is coupled to the elongated member 7400.

Figure 8:
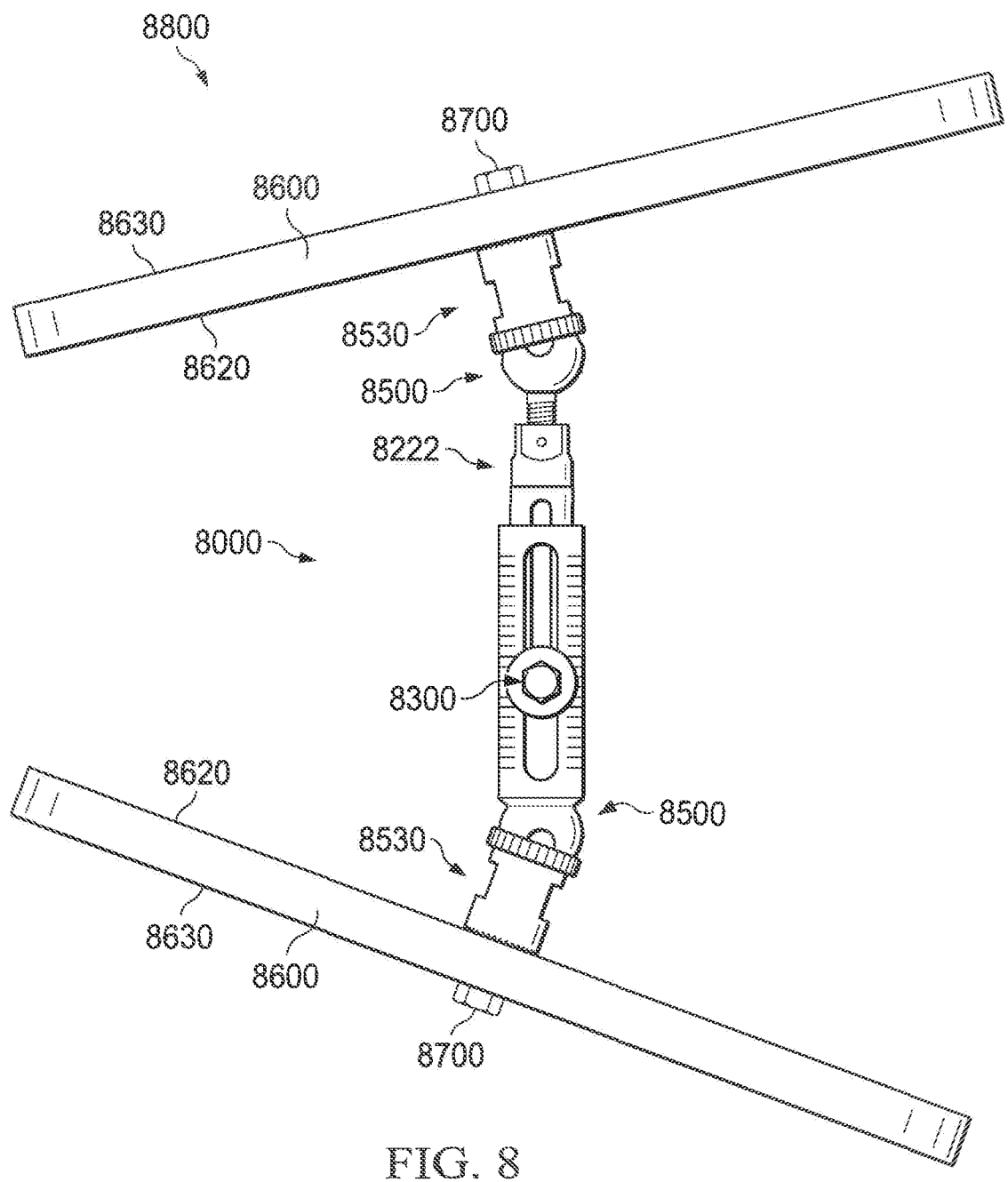
FIG. 8 illustrates a side view of a connecting rod coupled to an external fixation device according to a specific example embodiment of the disclosure.

FIG. 8 depicts an example embodiment of an external fixation assembly 8800 comprising two external fixation rings 8600 attached to a connecting rod 8000. The connecting members 8530 of the connecting rod 8000 may be coupled to first surfaces 8620 of the external fixation rings 8600 via connecting elements 8700 inserted from second surfaces 8630 of the external fixation rings 8600. After tightening of the connecting rod 8000 to the external fixation rings 8600 as described in FIG. 1A, the rotation of the joints 8500 of the connecting rod 8000 may be inhibited, such that the external fixation rings 8600 are held in a rigid (e.g., non-parallel, as illustrated) configuration. Such rigidity of the external fixation assembly 8800 may be desirable in treatment scenarios, e.g., in order to avoid patient discomfort and/or healing site perturbation. After attachment of the connecting rod to the external fixation rings 8600, gradual and/or rapid adjustment of the positional offset of the external fixation rings 8600 can be realized via the gradual adjustment mechanism 8222 and/or fastener 8300, respectively. However, in practice it may only be desired to adjust the length via the gradual adjustment mechanism 8222 and keep the fastener tightened after attachment to the external fixation rings 8600. For example, it may be difficult to lengthen the connecting rod 8000 by a direct translation after loosening the fastener 8300 for a fairly rigid external fixation assembly 8800, e.g., due to other connection rods (not shown in FIG. 8) holding the external fixation rings in place. On the other hand, the twistable lengthening process provided by the gradual adjustment mechanism 8222 may facilitate adjustment of rigidly-positioned external fixation rings, e.g., due to the slight length change per turn.

Before attachment of the connecting rod 8000 to the external fixation rings, the gradual adjustment mechanism 8222 configuration and fastener 8300 position may be set to desired lengths. For example, if it is believed that the external fixation rings 8600 will be increased in positional offset after attachment of the connecting rod 8000, the gradual adjustment mechanism 8222 may be configured to allow for a large range of length expansion (e.g., by positioning the distal joint 8500 close to the gradual adjustment mechanism 8222), and the fastener may be positioned complementarily to compensate for the length change due to the gradual adjustment mechanism 8222 configuration.

For female joints 8500 (as illustrated), the connecting member may be a screw inserted through a second, non-coupling surface 8630 of the external fixation ring 8600. For male joints (not shown), the connecting member may be a nut operable to threadably couple with a portion of the connecting member insert protruding through the external fixation ring, on the second, non-coupling surface 8630.

It will be understood that connecting members 8530 not comprising connecting member housings may be used, but such embodiments may forgo the benefits of connecting member housings, such as joint 8500 rotation inhibition.

Figure 9:
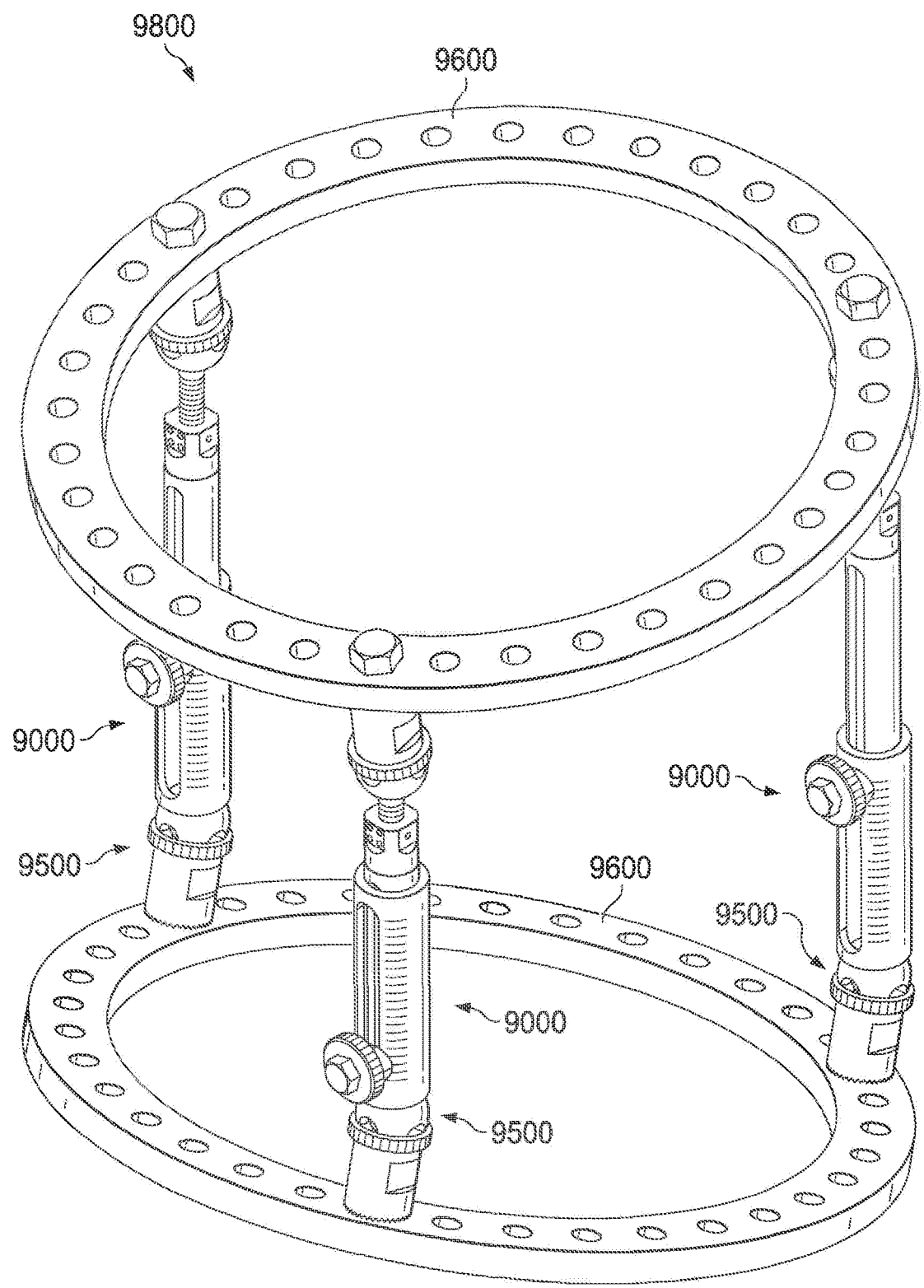
FIG. 9 illustrates a perspective view of a connecting rod coupled to an external fixation device according to a specific example embodiment of the disclosure.

FIG. 9 depicts a further example embodiment of an external fixation assembly comprising two external fixation rings 9600 and multiple connecting rods 9000 attached to each of the external fixation rings 9600. The multiple connecting rods 9000 provide greater stability and rigidity of the relative position and orientation of the external fixation rings 9600. Additionally, though not shown, further bone pins, bone wires, external fixation rings, and/or connecting rods may be present in an external fixation assembly 9800. As illustrated, not all the connecting rods 9000 may be configured at the same length, depending on the desired external fixation assembly 9800 configuration of the external fixation rings 9600.

During installation of the external fixation rings, braces (not shown) may be utilized to hold the external fixation rings 9600 in place until the connecting rods 9000 are attached. The braces may be temporarily clipped onto the external fixation rings 9600.

During installation and/or removal of the connecting rods 9000, it may be advantageous for the connecting rods 9000 to comprise at least one female joint 9500 in order to not constrain a connecting rod 9000 to being removed from the external fixation ring 9600 about an axis of insertion corresponding to the lengthwise axis of the axial bore of the connecting member, as would be required for a male joint, so as to avoid perturbation of the external fixation rings 9600 during installation and/or removal of the connecting rod 9000. Male joints may necessarily perturb the external fixation rings 9600 due to limited range of motion of the other joint of the connecting rod.

In general, it will be understood that the descriptors "proximal" and "distal" may be interchanged without loss of operability. Further, in general the connecting rod may comprise stainless steel, heat tempered and hardened stainless steel, and/or titanium. Alternatively or additionally, the connecting rod may comprise plastics such as nylon, peek, techtron, torlon, etc. (e.g., for a gradual adjustment mechanism). In some embodiments, at least a portion of the connecting rod may be manufactured with rolled threads. Threads of an elongated member 7400 may be formed up to the base of a coupled rotatable member housing 7510 in order to maximize the translation range of the elongated member 7400 with respect to an inner sleeve 7200. Whether or not external threads of an elongated member 7400 are formed up to the base of a coupled rotatable member housing 7510, at least a portion between the external threads of the elongated member 7400 and the base of a rotatable member housing 7510 may be relieved, undercut, and/or of a narrower diameter, e.g., in order to prevent damage to the internal threads 7226 of an internal sleeve that is translated to and/or near that portion of the elongated member 7400 (e.g., when "fully shortened and/or retracted). Alternatively or additionally, a stopper and/or spacer may be positioned near the base of a rotatable member housing 7510 and/or near a distal end 7220 of an inner sleeve to limit the translational shortening and/or retraction of the elongated member 7400 with respect to the inner sleeve 7200.

In some embodiments, it may be advantageous to have at least one female attachment (or "joint") on at least one end of a connecting rod. For example, a female attachment may allow for a shorter overall minimum length of the connecting rod relative to a connecting rod with two male attachments. A shorter overall minimum length may be advantageous for insertion and/or removal of connecting rods (e.g., in the case of a rigid external fixation assembly and/or a hexapod strut arrangement). A female attachment may also allow for easier insertion and/or removal of a connecting rod with respect to an external fixation assembly (or external fixation rings thereof) by at least partially obviating the need for rotational freedom of connecting rod joints during insertion and/or removal (e.g., removal of a male connecting member from an external fixation ring may require a gradually changing joint angle as the male connecting member is removed, but connecting rod joint(s) may not be able to support such angles). Further, a female attachment may be advantageous when neighboring hole(s) (for connecting member and/or connecting element insertion) are occupied (e.g., by wire fixation or half pin fixation bolts). For example, it may be difficult to secure a male connecting member with another connecting component (e.g., a nut) on the opposite side of the fixation ring, whereas a female attachment may be coupled with a bolt that is pre-inserted through the fixation ring.

The present disclosure also includes embodiments for maintaining the orientation of first and second fixator rings for immobilizing bone segments. One exemplary embodiment includes providing a connecting rod comprising a telescopic housing having an axial bore defined therethrough; an adjustment sleeve slidably disposed within the axial bore, the adjustment sleeve and the telescopic housing; and an externally threaded elongated member threadably coupled the adjustment sleeve. A first joint is coupled to an end portion of the housing, and a first rotating member is received in the first joint. Furthermore, the first rotating member comprises a first connection mechanism operable to releasably couple the first rotating member to the first fixator ring and substantially limit the rotational movement of the first rotating member. A second joint is coupled to an end portion of the housing, and a second rotating member is received in the second joint. Furthermore, the second rotating member comprises a second connection mechanism operable to releasably couple the second rotating member to the second fixator ring and substantially limit the rotational movement of the second rotating member. The disclosed embodiment further includes adjusting the longitudinal position of adjustment sleeve relative to the telescopic housing, and releasably coupling the adjustment sleeve to the telescopic housing using a sleeve fastener. The disclosed embodiment further includes using the first connection mechanism to releasably couple the first rotating member to the first fixator ring and substantially limit the rotational movement of the first rotating member, and using the second connection mechanism to releasably couple the second rotating member to the second fixator ring and substantially limit the rotational movement of the second rotating member.

The methods of the present disclosure may be performed with a subject, e.g., a human or another vertebrate animal. One or more bones (of the subject) to be fixed may be selected. Any suitable bone(s) may be selected, such as a long bone(s) and/or at least a pair of bones connected via an anatomical joint. Exemplary bones include leg bones (femur, tibia, and fibula), arm bones (humerus, radius, and ulna), foot bones (calcaneus, talus, metatarsals, and phalanges), wrist/hand bones (carpals, metacarpals, and phalanges), etc. In exemplary embodiments, one or more bones including at least one long bone may be selected.

An external fixation device may be constructed along and at least partially around the selected bone(s). The external fixation device may include a plurality of rings fixed in position relative to one another by numerous connecting rods secured to the rings.

The external fixation device may be connected to the selected bone(s). Connection may be performed at any suitable time, such as before, during, and/or after construction of the external fixation device. For example, the external fixation device may be assembled and then connected to bone, or individual external fixation device members or external fixation device sub-assemblies may be connected to the bone before the external fixation device is fully assembled. Connection of the external fixation device to bone may include placing connectors, such as wires, pins, screw, and/or rods, among others, through the skin and into, through, and/or around the selected bone.

The external fixation device may be reconfigured while it is connected to the one or more selected bones. Reconfiguration may include adjusting the length, angle, position, and/or connection site of one or more external fixation device components, particularly connecting rod. In some embodiments, reconfiguration may involve lengthening and/or shortening one or more (or all) connecting rods of the external fixation device. In some embodiments, reconfiguration may involve replacing one or more connecting rods with a different connecting rod(s). The different connecting rod may be of different size, pivotability, adjustability, shape, and/or the like.

The external fixation device may be braced to facilitate reconfiguration. Bracing the external fixation device may stiffen and/or stabilize the external fixation device such that reconfiguration produces fewer undesired changes to the external fixation device structure as the external fixation device is weakened and altered during reconfiguration. Bracing may be performed by a pair of connecting rods of the external fixation device. In some examples, the brace may be configured to be clipped onto the external fixation device members before the brace is fully secured to the external fixation device members. For example, the brace may include one or more external fixation device engagement elements that are biased to opposingly engage one or more respective external fixation device members. In any case, each engagement element may be secured in place on the external fixation device member by operating a user control, manually or with a tool. Furthermore, the relative spacing and angular disposition of the engagement elements may be fixed by operating a user control, either the same user control(s) for securing the engagement element to a frame member or a distinct user control.

In some examples, the brace may include one or more movable joints, and the brace may be installed in engagement with the external fixation device members with one or more of the joints in a movable configuration. The movable joints then may be adjusted to a locked (fixed) configuration. Alternatively, or in addition, the brace may include a plurality of movable joints and one or more of the movable joints may be locked before or during brace placement onto the frame, and one or more other of the movable joints may be locked after brace placement onto the external fixation device.

The brace may be removed after frame reconfiguration. Accordingly, the brace may be installed with the frame (and connecting rod) fixing bone and removed with the frame reconfigured and still fixing bone. The brace thus may be present on the external fixation device for only a fraction of the time that the external fixation device is fixing bone.

It is contemplated that any embodiment discussed in this specification can be implemented with respect to any method, kit, reagent, or composition of the disclosure, and vice versa. Furthermore, compositions of the disclosure can be used to achieve methods of the disclosure.

Persons skilled in the art may make various changes in the shape, size, number, and/or arrangement of parts without departing from the scope of the instant disclosure. For example, the position and number of joints or joint components may be varied. In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Such option may not be exercised and, indeed, in some embodiments, disclosed systems, compositions, apparatuses, and/or methods may exclude any other features or steps beyond those disclosed herein. Elements, devices, methods, and method steps not recited may be included or excluded as desired or required. Persons skilled in the art may make various changes in methods of preparing and using a device and/or system of the disclosure. For example, a device and/or system may be prepared and or used as appropriate for animal and/or human use (e.g., with regard to sanitary, infectivity, safety, toxicity, biometric, and other considerations).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100. Disclosed percentages are weight percentages except where indicated otherwise.

All or a portion of a device and/or system for a connection rod may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

The title, abstract, background, and headings are provided in compliance with regulations and/or for the convenience of the reader. They include no admissions as to the scope and content of prior art and no limitations applicable to all disclosed embodiments.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure include preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

The invention claimed is:

1. A connecting rod for an external fixation device, the connecting rod comprising:
   a first joint comprising:
      a first rotatable member housing;
   a first rotatable member disposed within the first rotatable member housing, the first rotatable member having a first bore; and
      a first connecting member comprising a first connecting member insert having a stem partially disposed within the first bore of the first rotatable member;
      wherein the first connecting member insert comprises a second bore; and wherein the second bore is operable to receive a connecting element from a first external fixation ring.

2. The connecting rod of claim 1, wherein the first rotatable member housing comprises one or more grooves, and the stem of the first connecting member insert is disposed through the one or more grooves, thereby limiting rotation of the first rotatable member in a first direction about the first joint while allowing a greater range of motion in a second direction about the first joint; and
wherein rotational movement of the first rotatable member is limited upon fixation of the first connecting member to the first external fixation ring.

3. The connecting rod of claim 1, wherein the first connecting member further comprises a first connecting member housing comprising a first aperture and a non-circular cavity, and wherein the first connecting member insert further comprises a non-circular portion operable to couple with the non-circular cavity to prevent rotation of the first connecting member insert with respect to the first connecting member housing.

4. The connecting rod of claim 3, wherein the first connecting member housing comprises at least one of a tool manipulation facilitator and a manual manipulation facilitator.

5. The connecting rod of claim 3, wherein the first connecting member housing comprises a coupling facilitator on a coupling end of the first connecting member housing.

6. The connecting rod of claim 3, wherein the first connecting member housing comprises a base and an inner recessed portion near the base, the inner recessed portion formed complementarily to the first rotatable member housing.

7. The connecting rod of claim 1, wherein the first rotatable member is inserted into the first rotatable member housing through an end of the first rotatable member housing opposite the first connecting member housing.

8. The connecting rod of claim 1, wherein the first connecting member insert is threadedly coupled with the first bore of the first rotatable member.

9. The connecting rod of claim 1, wherein the first rotatable member comprises an at least partially spherical outer surface and the first rotatable member housing comprising a corresponding inner surface.

10. The connecting rod of claim 1, further comprising:
a second joint comprising:
a second rotatable member housing;
a second rotatable member disposed within the second rotatable member housing, the second rotatable member having a third bore; and
a second connecting member coupled with the second rotatable member, wherein the second connecting member is operable to couple with a second external fixation ring;
wherein the second connecting member comprises a second connecting member insert having a stem partially disposed within the third bore of the second rotatable member, the second connecting member insert comprising a fourth bore, and wherein the fourth bore is operable to receive a connecting member from the second external fixation ring.

11. A system for external fixation, comprising:
at least one rod including a first joint comprising:
a first rotatable member housing;
a first rotatable member disposed within the first rotatable member housing, the first rotatable member having a first bore; and
a first connecting member comprising a first connecting member insert having a stem partially disposed within the first bore of the first rotatable member;
wherein the first connecting member insert comprises a second bore; and
wherein the second bore is operable to receive a connecting element from a first external fixation ring;
the first external fixation ring; and
a second external fixation ring couplable to an end of the rod opposite the first joint.

12. The system of claim 11, wherein the at least one rod further includes a second joint comprising:
a second rotatable member housing;
a second rotatable member disposed within the second rotatable member housing, the second rotatable member having a third bore; and
a second connecting member coupled with the second rotatable member, wherein the second connecting member is operable to couple with the second external fixation ring, and wherein the second connecting member comprises a second connecting member insert having a stem partially disposed within the third bore of the second rotatable member.

13. The system of claim 12, wherein the at least one rod further includes:
a telescoping housing secured to the first rotatable member housing; and
an inner sleeve secured to the second rotatable member housing;
wherein the inner sleeve is configured to linearly translate within the telescoping housing to lengthen or shorten the at least one rod.

14. A connecting rod for an external fixation device, the connecting rod comprising:
a first joint comprising:
a first rotatable member housing;
a first rotatable member disposed within the first rotatable member housing, the first rotatable member having a stem extending therefrom; and
a first connecting member comprising a first connecting member insert secured to the stem;
wherein the first connecting member insert comprises a bore operable to receive a connecting element from a first external fixation ring to secure the connecting rod to the first external fixation ring.

15. The connecting rod of claim 14, further comprising:
a telescoping housing extending from first rotatable member housing; and
an inner sleeve at least partially receivable within the telescoping housing;
wherein a length of the connecting rod is adjustable by linear translation of the inner sleeve with respect to the telescoping housing.

16. The connecting rod of claim 15, further comprising:
a second joint secured to the inner sleeve on an end of the inner sleeve opposite the first joint.

17. The connecting rod of claim 16, wherein the second joint comprises:
a second rotatable member housing;
a second rotatable member disposed within the second rotatable member housing, the second rotatable member having a second stem extending therefrom; and
a second connecting member comprising a second connecting member insert secured to the second stem, wherein the second connecting member insert comprises a bore operable to receive a connecting element from a second external fixation ring to secure the connecting rod to the second external fixation ring.

18. The connecting rod of claim 17, wherein the first connecting member comprises a first connecting member housing comprising a first non-circular cavity, the first connecting member insert comprises a first non-circular portion operable to couple with walls of the first non-circular cavity to prevent rotation of the first connecting member insert with respect to the first connecting member housing, and wherein the second connecting member comprises a second connecting member housing comprising a second non-circular cavity, the second connecting member insert comprises a second non-circular portion operable to couple with walls of the second non-circular cavity to prevent rotation of the second connecting member insert with respect to the second connecting member housing.

19. The connecting rod of claim 18, wherein the first rotatable member comprises an at least partially spherical outer surface and the first rotatable member housing comprises a corresponding inner surface, and wherein the second rotatable member comprises an at least partially spherical outer surface and the second rotatable member housing comprises a corresponding inner surface.

20. The connecting rod of claim 14, wherein the first rotatable member comprises an at least partially spherical outer surface and the first rotatable member housing comprises a corresponding inner surface.

* * * * *